United States Patent [19]

Albarella et al.

[11] Patent Number: 4,954,451

[45] Date of Patent: Sep. 4, 1990

[54] AGENT FOR DIMINISHING ASCORBATE INTERFERENCE IN REAGENT SYSTEMS AND METHOD RELATING THERETO

[75] Inventors: James P. Albarella; Mietak T. Yip, both of Elkhart, Ind.

[73] Assignee: Miles Inc., Elkhart, Ind.

[21] Appl. No.: 371,253

[22] Filed: Jun. 26, 1989

[51] Int. Cl.$^5$ .................. G01N 1/00; G01N 33/00; G01N 33/72

[52] U.S. Cl. ........................... 436/175; 436/66; 436/95; 436/904

[58] Field of Search ............... 436/175, 66, 95, 904, 436/82; 435/28; 422/57

[56] References Cited

U.S. PATENT DOCUMENTS

| | | | |
|---|---|---|---|
| 3,411,887 | 11/1968 | Ku | 422/57 X |
| 4,288,541 | 9/1981 | Magers | 436/175 |
| 4,310,626 | 1/1982 | Burkhardt | 436/66 |
| 4,587,220 | 5/1986 | Mayambala-Mwanika | 436/175 |
| 4,743,559 | 5/1988 | Koevér | 436/175 |
| 4,755,472 | 7/1988 | Ismail | 436/66 |

OTHER PUBLICATIONS

*CRC Handbook of Physics and Chemistry*, 46th ed., CRC Publishing: Cleveland, Ohio, 1965, p. B-165.

*Primary Examiner*—Robert J. Warden
*Assistant Examiner*—Thalia P. Vassilatos
*Attorney, Agent, or Firm*—Roger N. Coe

[57] ABSTRACT

The present invention is directed to an agent and method for eliminating ascorbate interference in reagent systems, particularly assay systems using oxidase/peroxidase coupled reactions or similar type redox chemistry. The present invention can also be used in reagent systems involving enzyme/substrate reactions in which the substrate is sensitive to reductants such as ascorbate. The agents of this invention comprise water insoluble cerium (IV) compounds.

2 Claims, 1 Drawing Sheet

AGENT FOR DIMINISHING ASCORBATE INTERFERENCE IN REAGENT SYSTEMS AND METHOD RELATING THERETO

BACKGROUND OF THE INVENTION

I. Field of the Invention

The present invention is directed to an agent and method for eliminating ascorbate interference in reagent systems, particularly assay systems using oxidase/peroxidase coupled reactions or similar type redox chemistry. The present invention can also be used in reagent systems involving enzyme/substrate reactions in which the substrate is sensitive to reductants such as ascorbate. Thus, the present invention can be used to remove interference of ascorbate in analyte detection systems for the determination of glucose, occult blood, cholesterol, triglycerides and uric acid, as well as other analytes. More specifically, the agent and method of this invention comprise the use of water insoluble cerium (IV) compounds.

II. Discussion of the Prior Art

Ascorbic acid is an important and well known nutrient which exists naturally in many foods, such as fruits and vegetables, and which can also be synthesized inexpensively as a food additive or vitamin supplement. As a result, ascorbic acid is relatively plentiful and the general population tends to ingest more ascorbic acid than necessary.

Excess ascorbic acid is generally not harmful because the body will only absorb ascorbic acid in an amount sufficient to meet the body's short term needs, quickly disposing of the excess by means of the body's urinary system. As a result, ascorbic acid is often found in urine samples used in medical analysis.

Unfortunately, ascorbic acid in urine can be an unwanted interferant for many urine assays presently in existence. Urine assays in general are important medical tools in diagnosing and treating the general population and therefore much attention has been focused upon this problem in recent years.

Urine assays often comprise redox indicator and these indicators are generally incorporated into the assay system in their reduced form. The indicators will change color when oxidized and are therefore called "redox" indicators, because they change color as they move from a reduced to an oxidized state due to the presence of an oxidizer.

In many assay systems an analyte of interest will directly or indirectly cause the oxidation of the assay's redox indicator, thereby causing a detectable response which correlates with the presence of the analyte. In other words, when the appropriate analyte is added to the assay system the redox indicators will undergo the following reaction:

$$I_{red} \rightarrow I_{ox} + \text{at least 1 electron}$$

wherein $I_{red}$ is the indicator in a reduced state (negative color response) and wherein $I_{ox}$ is the indicator in an oxidized state (positive color response).

However, ascorbic acid in solution undergoes the following reaction:

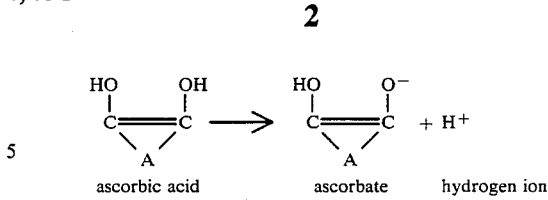

where A is defined as $C_4H_6O_4$. Ascorbate is a reductant, because it is able to donate an electron and thereby reduce the substance receiving the electron:

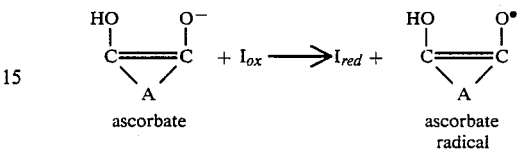

In this way, ascorbate can interfere with a redox indicator by reducing the indicator when it is in its oxidized form, thereby inhibiting the intended color change and causing a "false negative."

Numerous methods have been tried, some successfully, which eliminate the adverse affect ascorbic acid can have upon redox indicators in an assay system. One successful method is disclosed in U.S. Pat. No. 4,587,220 by Mayambala-Mwanika, et al., whereby ferric complexes are combined with hydroperoxide to act as an ascorbate scavenger. This scavenger system prevents ascorbate reduction of redox indicators.

In Mayambala, $Fe^{+3}$ is complexed with an iron chelate, such as HEDTA (N-2-hydroxyethylethylenediaminetriacetic acid), and reacted with ascorbic acid. The Fe(III) chelate scavenges ascorbic acid as follows:

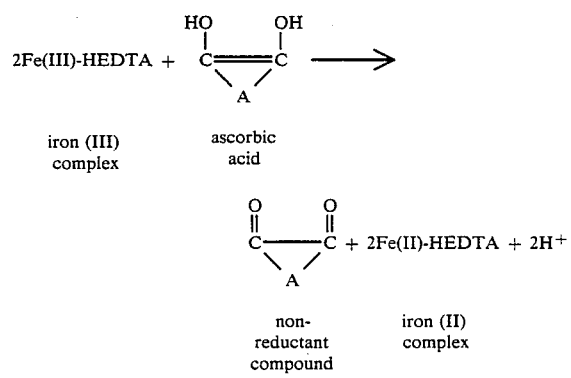

The Mayambala scavenger causes the secondary alcohol groups in ascorbic acid to be oxidized into ketones and in this way ascorbic acid is transformed into a nonreductant compound which will not interfere with a redox indicator system. However, the Fe(II)-HEDTA is recycled back into Fe(III)-HEDTA using a peroxide or hydroperoxide as follows:

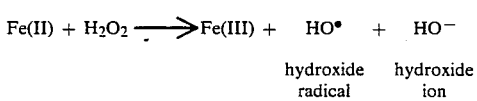

The resulting hydroxide radical can receive an electron according to the following reaction:

HO· + 1 electron → HO⁻ and can therefore act as an oxidizer. As a result, the hydroxide radical can oxidize the redox indicator when the indicator is in its reduced (original) form, thereby causing a color change regardless of whether or not an analyte of interest is present. Consequently, in preventing a false negative due to ascorbic acid, the ascorbic acid scavenger system of Mayambala can cause an unwanted false positive. In solving one problem, the ascorbic acid scavenger system creates another.

The Mayambala patent suggests an adjustment of the assay's pH by means of conventional buffers to minimize the oxidation affect of the scavenger system. Indeed, since oxidation reactions are typically acid catalyzed and different oxidation reactions can involve different kinetic interactions it may be possible to find a pH which would accelerate indicator oxidation due to the analyte without substantially accelerating indicator oxidation due to the ascorbic acid scavenger system.

The Mayambala patent also suggests a dry phase format which separates the reagent system into two dip solutions. One dip solution is incorporated and dried on a support and thereafter the second dip solution is also incorporated and dried onto the support. Mayambala therefore suggests that certain constituents of a reagent system can perhaps be separated in a dry format in a manner where the desired oxidation reaction will dominate over the unwanted oxidation reaction.

However, pH adjustment may not prove to be advantageous for every reagent system and a multidip process for creating a dry phase system may not always be practical or workable for every reagent system. Furthermore, a liquid format may in some cases be more desirable than a dry phase format.

Consequently, it is an object of the present invention to provide a system whereby ascorbate or similar type reductant interference can be eliminated without adversely affecting the reliability of a redox indicator system.

A further object of the present invention is to provide an ascorbate resistant assay system which can be used in solution form or can be incorporated into a reagent strip using a one dip method.

Other objects and features of the present invention will become apparent to one of ordinary skill in the art upon the reading of the following specification, particularly the detailed description of the preferred embodiments and the claims.

III. Information Disclosure

Kaminagayoshi, et al, "A Container for Sample Analysis Based on Enzymic and Diazo Coupling Reactions", Japanese Patent Application No. 84/53478, 22 Mar. (1984), describes the use of a water resistant paper cup treated with a solution containing methylcellulose (2.5%) and NaIO₄ (10 mg/ml) as a device for determining urinary glucose substantially without ascorbic acid interference.

Tom, "Immunoassay"; European Patent Application No. EP 103 958, 28 Mar. 1984, discloses a reagent strip immunoassay in which a peroxidase is used to catalyze the formation of a detectable dye. A bibulous support is impregnated with periodate after immobilization of reagents to reduce or eliminate interference by ascorbate in samples.

"Method and Diagnostic Agents for the Detection of Redox Reactions," European Patent Application No. 0 037 056, 24 Mar. 1981, describes the use of iodate to oxidize ascorbic acid. The teaching specifically states that periodate cannot be used because it oxidizes most indicators in addition to ascorbic acid.

Tomioka, et al., "Cerium Catalyzed Selective Oxidation of Secondary Alcohols in the Presence of Primary Ones," *Tetrahedron Letters*, 23(5):539–542 (1982) describes the combination of $(NH_4)_2Ce(NO_3)_6$—$NaBrO_3$ or $Ce(SO_4)_2\cdot2H_2SO_4$—$NaBrO_3$ as effective reagents for selective oxidation.

Firouzabadi, et al., "Dinitratocerium (IV) Chromate Dihydrate, $[Ce(NO_3)_2]CrO_4\cdot2H_2O$, a Mild Reagent for the Oxidation of Organic Compounds in Organic Media", *Synthetic Communications*, 14(10):973–981 (1984), discusses the title compound's preparation and use for the oxidation of different organic substrates in benzene such as benzyl alcohol and diols.

Firouzabadi, et al., "Bis[trinitratocerium (IV)] Chromate, $[Ce(NO_3)_3]_2CrO_4$: A Mild Oxidant in Organic Synthesis", *Synthetic Communications*, 14(7):631–637 (1984) discusses the title compound's preparation and use in the oxidation of benzylic alcohols to aldehydes and ketones, α-hydroxyketones to diketones, hydroquinone to p-benzoquinone and catechol to o-benzoquinone.

Firouzabadi, et al., "Tris-trinitratocerium (IV) Paraperiodate $[(NO_3)_3Ce]_3H_2IO_6$, An Efficient and a Versatile Oxidant in Organic Synthesis"; *Synthetic Communications*, 14(11):1033–1042 (1984) discusses the title compound's preparation and use for the oxidation of different classes of organic compounds such as benzylic alcohols and diols in dry benzene with high yields.

Firouzabadi, et al., "Ceric Triethylammonium Nitrate $[Ce(Et_3NH)_2](NO_3)_6$ an Efficient Oxidant for the Oxidation of Benzylic Alcohols and α-hydroxy Ketones to Their Corresponding Carbonyl Compounds Under Mild Conditions", *Synthetic Communications*, 13(13):1143–1147 (1983) discusses the title compound's preparation and use for the oxidation of benzylic alcohols, and α-hydroxy ketones to their corresponding carbonyl compounds in methylene chloride with high yields.

Ho, "Cerium (IV) Oxidation With a Dual Oxidant System: Reaction of Some Arylmethanols"; *Synthesis*, 12, pp. 936 (1978) describes a dual oxidant system of Ce(IV)/bromate.

The above-identified citations relate generally to the chemistry of the present invention. However, none of these references teaches or suggests that the cerium(IV) compounds of the present invention can be used to selectively oxidize ascorbate, thereby eliminating ascorbate interference, without interfering with desired redox coupled reactions typically used in assay systems.

SUMMARY OF THE INVENTION

The present invention is directed to an agent and method for eliminating ascorbate interference in reagent systems, particularly assay systems using oxidase/peroxidase coupled reactions or similar type redox chemistry. The present invention can also be used in reagent systems involving enzyme/substrate reactions in which the substrate is sensitive to reductants such as ascorbate. The agent of this invention comprises water insoluble cerium (IV) compounds.

BRIEF DESCRIPTION OF THE DRAWING

Other and further objections, advantages and features of the invention will be apparent to those skilled in the art from the following detailed description thereof, taken in conjunction with the accompanying drawing in which.

DETAILED DESCRIPTION OF THE PREFERRED EMBODIMENTS

Figure 1:
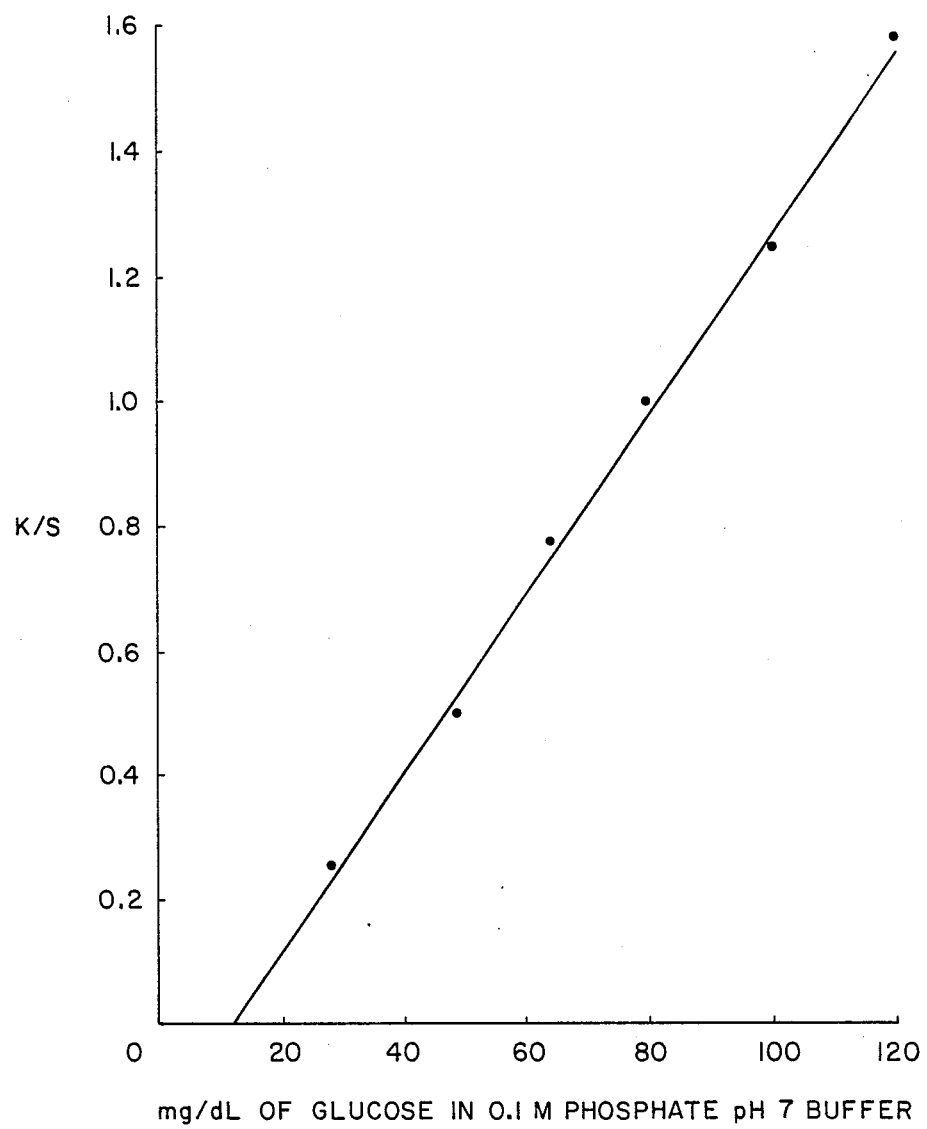
FIG. 1 is a graph illustrating a standard curve in accordance with Example II in which K/S is plotted against different concentrations of glucose.

Many detection systems using redox reactions are adversely affected by the presence of ascorbic acid. The present invention is directed to the use of water insoluble cerium IV compounds. In contrast to soluble ceric compounds, such as ceric nitrate, ceric sulfate, ceric ammonium nitrate (CAN), ceric triethyl ammonium nitrate (CTEN) and the like, insoluble ceric compounds, such as ceric hydroxide, ceric oxide, ceric fluoride, ceric iodate, tris(trinitratocerium)paraperiodate (TNCP), bis(trinitratocerium)chromate (BTCC), cerium acetylacetonate, cerium trifluoroacetylacetonate and pyridiniumhexachlorocerate, are useful in overcoming ascorbate interference. The compounds of this invention can be any water insoluble cerium IV compound. The concentration of such water insoluble cerium IV compounds in slurry form generally will range from about 5 to about 50 mM (millimolar) and, more particularly, from about 7 to about 37 mM. Concentrations below 5 mM are generally not effective while concentrations above about 50 can be effective but tend to offer no increased advantage.

The compounds of the invention selectively oxidize ascorbate, thereby eliminating ascorbate interference. The cerium IV oxidants of this invention are specific and typically do not produce any color development in the presence of a conventional redox indicator system. For example, the compound TNCP, identified in the Examples, can remove ascorbate interference of up to 250 milligrams per deciliter (mg/dL) of ascorbic acid present in a test sample within 10 seconds of mixing time. The fast and effective removal of ascorbate interference results in much improved accuracy in most assays using a oxidase/peroxidase coupled reaction and a redox indicator system.

The cerium IV oxidants of the present invention are not pH dependent. They are easily prepared and can be easily impregnated or immobilized onto a filter device to form a heterogeneous test system.

EXAMPLES

I. Synthesis of Water Insoluble Cerium IV Compounds (1) and (2) and a Water Soluble Cerium Compound (3)

Cerium (IV) oxidants were prepared according to the following procedures:

(1) Tris(trinitratocerium) Paraperiodate (TNCP)

Potassium periodate (4.6 gm, 20 mmole) was dissolved in 200 ml (milliliters) of warm deionized water. After allowing the solution to cool slightly, a solution of ceric ammonium nitrate (32.9 gm, 60 mmole) in 30 ml of deionized water was added dropwise over a period of 5 minutes. The resulting reaction mixture was then stirred at room temperature for 3 hours. A lemon colored solid separated out which was filtered, washed with deionized water twice, suspended in 100 ml of deionized water and freeze-dried to give 10.8 gm (grams) of a yellow solid (yield, 48%). Product prepared in this manner can be more easily resuspended in aqueous solution.

(2) Bis(trinitratocerium)chromate (BTCC)

Potassium dichromate (11.8 gm, 40 mmole) was dissolved in 200 ml of deionized water and then a solution of ceric ammonium nitrate (21.9 gm, 40 mmole) in 60 ml of deionized water was added dropwise over a period of 10 minutes. An orange solid separated out immediately. After stirring for 2 hours at room temperature the reaction mixture was filtered and washed with deionized water three times. The solid was then resuspended in 50 ml of deionized water and freeze-dried to give 14.3 gm of an orange solid (yield 92%).

(3) Ceric Triethylammonium Nitrate (CTEN)

Ceric hydroxide (10.4 gm, 50 mmole) was dissolved in 35 ml of nitric acid with heating. The solution was allowed to cool slightly and triethylamine (20.9 ml, 150 mmole) was added dropwise over a period of about 5 minutes. The resulting reaction mixture was stirred at room temperature for 3 hours and then cooled in an ice bath. The resulting orange precipitate was filtered, washed quickly with deionized water, and recrystallized from hot water to give 4 gm of orange solid, mp 135° C. (yield 11%)

II. Using Water Insoluble Cerium IV Compounds To Prevent Ascorbate Interference Low range glucose pads were made by impregnating Whatman 54 paper in two dip solutions. The first dip consists of 100 mM (millimolar) tetramethylbenzidine (TMB) and 0.5% Aerosol OT in 1-methoxy-2-propanol and the second dip solution consists of 250 units/ml of Sigma Type VII glucose oxidase, 500 units/ml peroxidase, 2% polyvinylpyrrolidone (PVP) K-60 and 0.01% FD&C yellow #5 in 0.2M morpholinoethane sulfonate, sodium salt (pH 6.0) as buffer.

Table I shows the results of how the ceric oxidants performed as ascorbic acid scavengers. A marked improvement of pad reactivity was observed when an oxidant is present as compared to those when no oxidant is used.

By way of comparison Table II shows the results of certain water-soluble ceric oxidants. It will be seen that in the absence of any glucose or ascorbic acid these soluble ceric oxidants provide a false positive result.

TABLE I

| Ascorbate Oxidant Systems | | | | |
|---|---|---|---|---|
| Oxidants | | Concentration mg/dL | | Relative[a] |
| Compounds | Concentration mM | Glucose | Ascorbic Acid | Reactivity |
| Control (no oxidant) | — | 0 | 0 | 0 |
| | | 100 | 0 | 100 |
| | | 100 | 50 | 7 |
| | | 100 | 100 | 0 |
| | | 100 | 200 | 0 |
| | | 100 | 250 | 0 |
| TNCP | 19 (suspension in water) | 0 | 0 | 0 |
| | | 100 | 0 | 100 |

TABLE I-continued

Ascorbate Oxidant Systems

| Compounds | Oxidants Concentration mM | Concentration mg/dL Glucose | Ascorbic Acid | Relative[a] Reactivity |
|---|---|---|---|---|
| | | 100 | 50 | 96 |
| | | 100 | 100 | 92 |
| | | 100 | 200 | 92 |
| | | 100 | 250 | 99 |
| BTCC | 19 | 0 | 0 | 0 |
| | (slurry in water) | 100 | 0 | 100 |
| | | 100 | 50 | 81 |
| | | 100 | 100 | 31 |
| | | 100 | 200 | 0 |
| | | 100 | 250 | 0 |
| CeO$_2$ | 19 | 0 | 0 | 0 |
| | (suspension in water) | 100 | 0 | 100 |
| | | 100 | 50 | 56 |
| | | 100 | 100 | 6 |
| | | 100 | 200 | 0 |
| | | 100 | 250 | 0 |
| | 105 | 0 | 0 | 0 |
| | (suspension in water) | 100 | 0 | 100 |
| | | 100 | 50 | 105 |
| | | 100 | 100 | 85 |
| | | 100 | 200 | 5 |
| | | 100 | 250 | 0 |
| | 151 | 0 | 0 | 0 |
| | (suspension in water) | 100 | 0 | 100 |
| | | 100 | 50 | 96 |
| | | 100 | 100 | 93 |
| | | 100 | 200 | 68 |
| | | 100 | 250 | 29 |
| Ce(OH)$_4$ | 19 | 0 | 0 | 0 |
| | (slurry in water) | 100 | 0 | 100 |
| | | 100 | 50 | 54 |
| | | 100 | 100 | 12 |
| | | 100 | 200 | 0 |
| | | 100 | 250 | 0 |
| | 91 | 0 | 0 | 0 |
| | (slurry in water) | 100 | 0 | 100 |
| | | 100 | 50 | 48 |
| | | 100 | 100 | 10 |
| | | 100 | 200 | 0 |
| | | 100 | 250 | 0 |
| | 167 | 0 | 0 | 0 |
| | (slurry in water) | 100 | 0 | 100 |
| | | 100 | 50 | 50 |
| | | 100 | 100 | 7 |
| | | 100 | 200 | 0 |
| | | 100 | 200 | 0 |
| | | 100 | 250 | 0 |

[a]The relative reactivity is calculated as percentage based on the reflectance in K/S of the solution containing 100 mg/dL of glucose and no ascorbic acid. The reflectance measurements were evaluated with a simplified form of the well-known Kubelka-Munk equation [see Gustav Kortum, "Reflectance Spectroscopy", pp. 106-111, Springer Verlag, NY (1969)]: K/S = (1 − R)$^2$/2R in which R is the fraction of reflectance from the test device, K is a constant and S is the light scattering coefficient of the particular reflecting medium.

TABLE II

| Compounds | Oxidants Concentration mM | Concentration mg/dL Glucose | Ascorbic Acid | Relative[a] Reactivity |
|---|---|---|---|---|
| CAN | 10 | 0 | 0 | 4 |
| | (solution in water) | 100 | 0 | 100 |
| | | 100 | 50 | 91 |
| | | 100 | 100 | 69 |
| | | 100 | 200 | 0 |
| | | 100 | 250 | 0 |
| | 19 | 0 | 0 | 9 |
| | (solution in water) | 100 | 0 | 100 |
| | | 100 | 50 | 102 |
| | | 100 | 100 | 100 |
| | | 100 | 200 | 32 |
| | | 100 | 250 | 0 |
| CTEN | 19 | 0 | 0 | 6 |
| | (solution in water) | 100 | 0 | 100 |
| | | 100 | 50 | 86 |
| | | 100 | 100 | 74 |
| | | 100 | 200 | 14 |
| | | 200 | 250 | 0 |

[a]The relative reactivity is calculated as percentage based on the reflectance in K/S of the solution containing 100 mg/dL of glucose and no ascorbic acid.

An assay device was developed comprising a filter plunger and a polypropylene test tube. A conventional assay reagent system is placed in the test tube together with a cerium IV oxidant. The filter plunger is pushed into the test tube to separate the solid cerium oxidant from the solution, thereby allowing for an analysis of the reagent system without interference by the nonsoluble cerium IV oxidant.

Experiments were conducted as follows: To a polypropylene test tube containing 100 μl (microliters) of 0.2M tris(trinitratocerium) paraperiodate suspension in water was added 1 ml of 0.1M phosphate (pH 7) containing 100 mg/dL of glucose and 100 mg/dL of ascorbic acid. The suspension was mixed for 5 seconds and then the filter plunger was pushed in. An aliquot of 50 μl was pipetted and diluted to 500 μl with 0.1M phosphate (pH 7) solution. Then 7 μl was pipetted onto a low range glucose pad and the reflectance at 600 nm (nanometers) wavelength was measured with a Seralyzer® reflectance photometer. The K/S at 60 seconds reaction was recorded. The Figure shows the results of the standard curve using solutions containing 0, 30, 50, 65, 80, 90, 100 and 120 mg/dL of glucose.

III. Performance of TNCP (Tris(trinitratocerium)paraperiodate)) in a Liquid Format The oxidant, TNCP, was screened in a liquid assay for its reactivities as ascorbic scavenger. The general procedures employed were as follows:

1. The oxidant was mixed with buffer solution in a 12×75 mm test tube.

2. Glucose and ascorbic acid solutions were added and the resulting material was mixed for about 10 seconds.

3. Glucose pads containing tetramethylbenzidine (TMB), glucose oxidase and peroxidase impregnated from a solution of 100 mM, 300 unit/mL and 500 unit/mL, respectively, in buffer, MES (4-morpholine ethane sulfonic acid), pH 6; paper: Whatman 54, were then dipped into the mixture and the color development rate was recorded.

4. Controls were run in which the oxidants or glucose or ascorbic acid were absent.

| Buffer | Phosphate, 0.4 M, pH 7 |
|---|---|
| Glucose | 100 mg/dL |
| Ascorbic Acid | 100 mg/dl |
| Oxidant | TNCP |

| Concentration of TNCP[a] | False Positive[b] | Reactivity[c] |
|---|---|---|
| 7 mM | — | very reactive |
| 19 mM | — | very reactive |

| -continued | | |
|---|---|---|
| 36 mM | — | very reactive |

[a] in a slurry form
[b] false positive tests were performed where both glucose and ascorbic acid were absent
[c] reactivity is measured within 10 seconds after mixing.

Thus, from the foregoing, it will be seen that this invention is well adapted to obtain all of the objectives of the invention as well as many other advantages with detection systems using redox reactions which are interfered with by ascorbic acid. The oxidant systems are very fast and effective. For example, TNCP can remove the interference of up to 250 mg/dL of ascorbic acid present in a test sample within 10 seconds of mixing time. Secondly, the oxidant systems are specific. Water insoluble oxidants like TNCP and BTCC do not react with the indicator tetramethylbenzidine to produce color in the absence of glucose. The more water soluble ceric oxidants such as CAN and CTEN give less than 10% color development in the absence of glucose. An additional advantage of the present invention is the fact that effective removal of ascorbate interference results in improved accuracy for the determination of glucose in the test solution. Additionally, the oxidant systems of the present invention are not pH dependent. Moreover, the oxidants are easily prepared and can be easily impregnated or immobilized onto a filter device for a heterogeneous test system.

Obviously, many other modifications and variations of the invention as hereinbefore set forth can be made without departing from the spirit and scope thereof and, therefore, only such limitations should be imposed as are indicated by the appended claims.

What is claimed is:

1. A method for substantially eliminating ascorbate interference in a reagent system, said method comprising:

combining a reagent system containing a redox indicator with a water insoluble cerium IV compound.

2. The method of claim 1 wherein the cerium IV compound is a member of the group consisting of:
   (a) Tris(trinitratocerium) Paraperiodate,
   (b) Bis(trinitratocerium)chromate,
   (c) Ceric fluoride,
   (d) Ceric hydroxide,
   (e) Ceric oxide, and
   (f) Ceric iodate.

* * * * *